US008842805B2

(12) United States Patent
Proksa

(10) Patent No.: US 8,842,805 B2
(45) Date of Patent: Sep. 23, 2014

(54) X-RAY EXAMINATION DEVICE AND METHOD

(75) Inventor: Roland Proksa, Neu Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 293 days.

(21) Appl. No.: 13/386,906

(22) PCT Filed: Jul. 20, 2010

(86) PCT No.: PCT/IB2010/053304
§ 371 (c)(1),
(2), (4) Date: Jan. 25, 2012

(87) PCT Pub. No.: WO2011/013031
PCT Pub. Date: Feb. 3, 2011

(65) Prior Publication Data
US 2012/0121063 A1     May 17, 2012

(30) Foreign Application Priority Data

Jul. 29, 2009    (EP) .................................... 09166693

(51) Int. Cl.
*A61B 6/03*    (2006.01)
*A61B 6/00*    (2006.01)
*G01T 1/17*    (2006.01)

(52) U.S. Cl.
CPC ............. *A61B 6/405* (2013.01); *A61B 6/4241* (2013.01); *A61B 6/482* (2013.01); *A61B 6/4233* (2013.01); *A61B 6/542* (2013.01); *G01T 1/171* (2013.01); *A61B 6/4021* (2013.01); *A61B 6/585* (2013.01); *A61B 6/032* (2013.01)
USPC .......................................... 378/16; 378/98.8

(58) Field of Classification Search
CPC ............................ A61B 6/486; A61B 6/542

USPC ........ 378/16, 98.8; 250/207, 370.09; 382/270
See application file for complete search history.

(56) References Cited

U.S. PATENT DOCUMENTS

| | | | |
|---|---|---|---|
| 5,117,445 A | 5/1992 | Seppi et al. | |
| 5,550,889 A | 8/1996 | Gard et al. | |
| 5,696,807 A * | 12/1997 | Hsieh | 378/109 |
| 6,399,950 B1 * | 6/2002 | Kimura et al. | 250/370.09 |
| 7,332,724 B2 | 2/2008 | Hefetz et al. | |
| 2006/0104496 A1 | 5/2006 | Arenson et al. | |
| 2007/0023669 A1 | 2/2007 | Hefetz et al. | |
| 2007/0098139 A1 | 5/2007 | Hoffman et al. | |
| 2007/0116173 A1 | 5/2007 | Arenson et al. | |
| 2007/0206721 A1 | 9/2007 | Tkaczyk et al. | |

FOREIGN PATENT DOCUMENTS

| | | |
|---|---|---|
| JP | 2003209746 A | 7/2003 |
| WO | 2008155715 A2 | 12/2008 |
| WO | 2010070583 A1 | 6/2010 |

* cited by examiner

*Primary Examiner* — Hoon Song
*Assistant Examiner* — Danielle Fox

(57) ABSTRACT

The present invention relates to an X-ray examination device and a corresponding method. A fast and periodical modulation of the X-ray flux within each detection interval is performed having a low X-ray flux at the beginning of the detection interval to ensure that no detection channel is overloaded. With increasing the X-ray flux particularly the peripheral detection channels will rum into saturation, which is detected. A saturated detector channel is stopped from further detecting radiation, and the time of effective radiation detection without saturation is measured for correcting those detection signals. From all detection signals, after any correction of detection signals from saturated detection channels, an X-ray image can be reconstructed.

16 Claims, 3 Drawing Sheets

X-RAY EXAMINATION DEVICE AND METHOD

FIELD OF THE INVENTION

The present invention relates to an X-ray examination device and a corresponding method as well as a computer program. The invention relates particularly to an X-ray examination device and a corresponding method using a single- or multi-layer photon counting X-ray detectors operated under conditions of ultra-high X-ray fluxes, like, e.g., medical X-ray CT (Computed Tomography), pre-clinical CT, or CT for material inspection or security applications

BACKGROUND OF THE INVENTION

There is currently one main obstacle to overcome in the realization of a spectral CT scanner based on photon counting detectors: the count rate limitations of state-of-the-art detector systems to about 5-10 million counts per second and pixel. Conventional CT systems are optimized for short scanning times and are therefore operated at very high photon flux rates of about 1 billion counts per second and pixel. Thus, there is a discrepancy between the count rate of available detectors and the count rate required for CT systems.

This count rate problem is a severe burden for the application of photon counting detectors in CT. The count rate limitation in CT is mainly for X-rays at the object (e.g. patient) periphery and outside the object (called peripheral rays). The majority of rays passing the object are sufficiently attenuated to not overload a counting detector. Although the measure of rays outside the object are not important for the imaging task, the overload of detector readings in the peripheral areas creates severe image artefacts and cannot be accepted for clinical imaging. Both known concepts have severe disadvantages:

European patent application No. 08171898.3 (PH011734EP1), which has not yet been published, describes an X-ray examination device and a corresponding method according to which the source current of the X-ray source is modulated between at least two different source currents to obtain at least two detection data sets for at least two different X-ray fluxes, wherein the lowest X-ray flux is low enough to avoid overloading of the X-ray detector in the direct X-ray beam. An X-ray image is reconstructed from said at least two detection data sets, wherein the pixel values of the pixels of said X-ray image are reconstructed taking into account whether or not the higher X-ray flux resulted in an overloading of the X-ray detector at the respective detector cells. In this way, however, the angular sampling of both acquisition types (low flux, high flux) is reduced.

SUMMARY OF THE INVENTION

It is an object of the present invention to provide an X-ray examination device and a corresponding method as well as a computer program by which this problem can be resolved and by which, generally, the problems of high count rate in the construction of a spectral CT scanner based on photon counting can be overcome.

In a first aspect of the present invention an X-ray examination device is presented comprising:

an X-ray source for emitting an X-ray beam of X-ray radiation while rotating around an imaging region, an X-ray detector having a plurality of detector cells for detecting X-ray radiation emitted by said X-ray source and having passed through said imaging region and for outputting detection signals, a source control unit for modulating an X-ray flux during the detection intervals, starting at the beginning of a detection interval with an X-ray flux level that avoids saturation of the X-ray detector in the direct X-ray beam and thereafter increasing the X-ray flux, a detection control unit for evaluating said detection signals, the detection control unit comprising i) a saturation detection unit for detecting, during a detection interval, saturation at predetermined detector cells and/or groups of detector cells, ii) a detection stopping unit for stopping detection of X-ray radiation at saturated detector cells or groups of detector cells for the remaining time of the detection interval and iii) a time measuring unit for obtaining a time information indicating an effective time portion of the detection interval during which X-ray radiation has been detected without saturation, and a signal processing device for reconstructing an X-ray image based on the detection signals, wherein detections signals of detector cells and/or groups of detector cells at which detection of X-ray radiation has been stopped during a detection interval due to saturation are corrected using the time information.

In a further aspect of the present invention a corresponding method is presented.

In a still further aspect of the present invention a corresponding computer program is presented comprising program code means for causing a computer to control an X-ray examination device comprising an X-ray source for emitting an X-ray beam of X-ray radiation while rotating around an imaging region and an X-ray detector having a plurality of detector cells for detecting X-ray radiation emitted by said X-ray source and having passed through said imaging region, said computer program comprising program code means to control the X-ray examination device.

Preferred embodiments of the invention are defined in the dependent claims. It shall be understood that the claim method has similar and/or identical preferred embodiments as the claimed device and as defined in the dependent claims.

The present invention is based on the idea to perform a fast and, preferably, periodical modulation of the X-ray flux within each detection interval (also called sample interval). The X-ray flux is particularly modulated such that it starts with an X-ray flux level, which is so low that no saturation of the X-ray detector in the direct X-ray beam occurs, and the X-ray flux is increased thereafter during the remaining time of the detection interval. The X-ray flux level at the beginning of the detection interval thus ensures that no detector cell and no detector channel is initially overloaded. However, with increasing the X-ray flux some detector cells, in particular the detector cells at the peripheries of the X-ray detector will run into saturation.

The present invention is further based on the idea to provide means for detecting saturation at one or more detector cells and/or groups of detector cells (e.g. a group of detector cells at different peripheries of the detector) and to stop further detection of radiation at such saturated detector cells or groups of detector cells. In addition, the effective time without saturation is measured for those detector cells or groups of detector cells.

Finally, based on the acquired information, in particular the detection signals measured by non-saturated detector cells but also measured by saturated detector cells as well and the obtained time information of effective measurement without saturation, an X-ray image is reconstructed. For this reconstruction, however, the detection signals acquired from detector cells that have run into saturation are corrected beforehand using the respective time information of those detector cells.

Through the invention it can be achieved that detector cells which do not run into saturation during a detection interval perform a regular measurement and issue the "real" detection signal. Only detector cells which run into saturation during a detection interval are stopped from further measuring during the same detection interval, but their measurement is thereafter corrected. In total, less data are "lost" during measurement compared to the known devices and methods resulting in an increased image quality having also less image artifacts.

According to a preferred embodiment the source control unit is adapted for modulating the X-ray flux in such a manner that the X-ray flux continuously increases over time during a detection interval. For instance, the X-ray flux (and/or the source current) of the X-ray source can be modulated according to a saw-tooth like function. However, other modulation schemes of the X-ray flux (and/or of the source current) of the X-ray source are applicable.

One embodiment for fast X-ray flux modulation is described in WO 2008/155715 A2, which can be applied here as well and which is herein incorporated by reference. The method and device disclosed therein use a z-deflection in a rotating anode or a rotating frame tube, where the electron beam is deflected from a first focal spot region to a second focal spot region being formed on the anode. Only the electromagnetic beam generated in the first focal spot region contributes to the useful electromagnetic exposure beam, wherein the second focal spot region is designed to avoid emission of electromagnetic beams into the direction of a useful electromagnetic beam direction.

In another embodiment, the X-ray flux modulation can be achieved by modulating the source current provided to the X-ray source.

Preferably, the detector is a photon-counting detector, but also a sensitive integrating detector can be subject to overload so that the invention makes sense for such other detectors as well.

According to a further embodiment the detection control unit comprises a plurality of detection control units for a plurality of individual detector cells and/or groups of detector cells, in particular for individual detector cells and/or groups of detector cells at the peripheries of the X-ray detector. Even further, it is preferred that the detection control unit comprises a detection control sub-unit for each detector cell. These embodiments contribute to further increase the accuracy of the acquired detection signals and the reconstructed X-ray image. At least the detector cells which are likely to go into saturation should be provided with separate detection control units. However, it is also possible that all detector cells have their own detection control unit.

Advantageously, the saturation detection unit comprise a current measuring unit for measuring the detector current, in particular the mean detector current, at the output of a detector cell or a group of detector cells and a comparator for comparing the detector current to a reference current indicating saturation. Since the detector current depends on the measured X-ray flux, a simple comparator can be used to check if, for instance, the mean current of the individual detector cells exceeds a limit associated with a saturation of the detector cell.

There are further possibilities for implementing this function. For instance, the mean frequency of the digital count pulses could be checked, and if a maximum limit for the frequency is reached, saturation is given. Alternatively, the number of counts can be observed, and if a maximum, time-dependent count number is reached, saturation is given.

Preferably, the detection stopping unit is adapted for registering and/or evaluating a detection signal from a saturated detector cell or group of detector cells. In other words, at the moment when saturation at a detector cell or a group of detector cells is detected, the detection signal of the saturated detector cell or group of detector cells measured up to this moment is stored for further processing, but for the remaining time of the same detection interval no further measurement is made at those detector cells, i.e. the detection signals on those detector channels is no longer stored and/or evaluated. This provides the easiest measure to stop the measurement at saturated detector cells.

In a photon-counting detector there also exists the possibility to stop counting further photons and to make sure that the front-end electronics come into a state of saturation, which possibly have a negative effect on the next detection interval.

Further, in an embodiment the signal processing device is adapted for correcting a detection signal of a detector cell and/or a group of detector cells, in which detection of X-ray radiation has been stopped during a detection interval, by estimating the missing detection signal portion of the detection signal for the remaining time interval of the detection interval during which the X-ray radiation has not been detected, based on a known flux modulation function, the measured detection signal portion and the time information obtained for this detection signal. There are generally various ways for this correction, and the applied way depends on the way in which the flux is modulated during the detection intervals.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
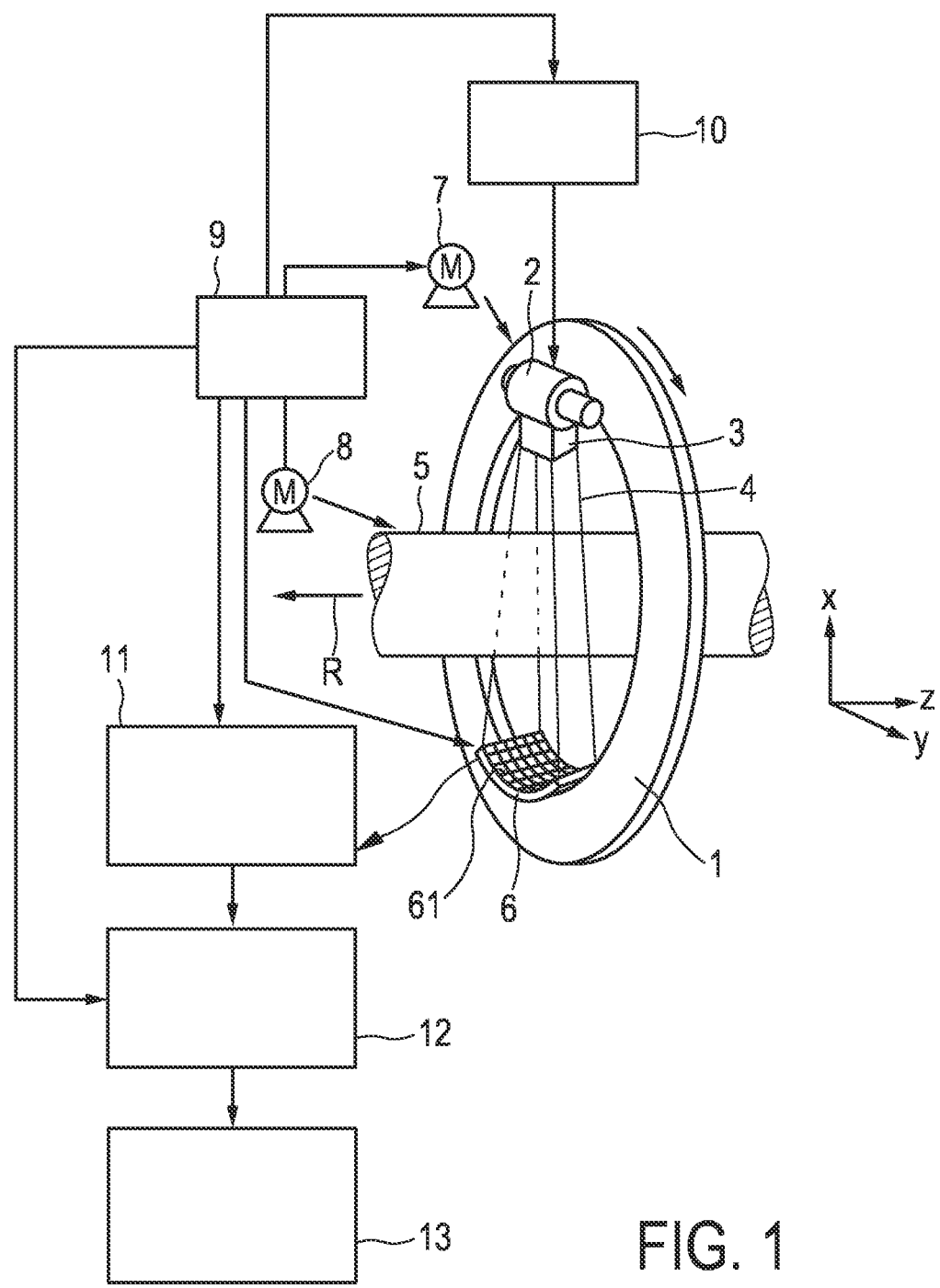
FIG. 1 shows an embodiment of an X-ray examination device in accordance with the present invention.

FIG. 1 shows a first embodiment of an X-ray examination apparatus according to the present invention, in particular a CT imaging system for medical applications and examination of a patient. The CT imaging system shown in FIG. 1 includes a gantry 1 which is capable of rotation about an axis of rotation R which extends parallel to the z direction. The radiation source 2, in particular a (conventional) polychromatic X-ray tube for emitting a broad energy spectrum of X-rays, is mounted on the gantry 1. The X-ray tube 2 is provided with a collimator device 3 which forms a conical radiation beam 4 from the radiation produced by the X-ray tube 2. The radiation traverses an object (not shown), such as a patient, in a region of interest in a cylindrical examination zone (imaging region) 5. After having traversed the examination zone 5, the X-ray beam 4 is incident on a X-ray detector unit 6, in this embodiment a two-dimensional photon-counting detector having a plurality of detector cells 61, which is mounted on the gantry 1 and which converts incident X-ray radiation into detection signals.

The gantry 1 is driven at a preferably constant but adjustable angular speed by a motor 7. A further motor 8 is provided for displacing the object, e.g. the patient who is arranged on a patient table in the examination zone 5, parallel to the direction of the axis of rotation R or the z axis. These motors 7, 8 are controlled by a control device 9, for instance such that the radiation source 2 and the examination zone 5 move relative to one another along a helical trajectory. However, it is also possible that the object or the examination zone 5 is not moved, but that only the X-ray source 2 is rotated.

Figure 6:
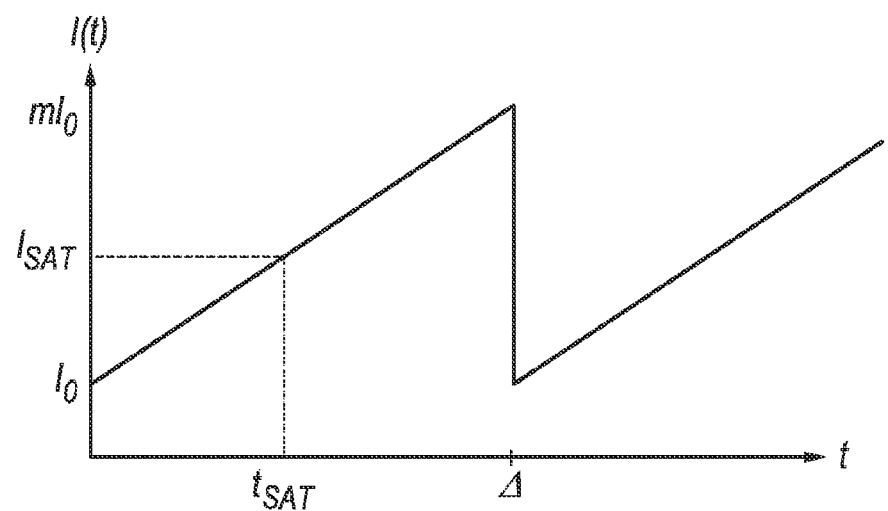
FIG. 6 shows a schematic diagram of an embodiment of a X-ray flux modulation function.

For controlling the X-ray source 2, in particular for modulating the X-ray flux that is provided by said X-ray source 2, a source control device 10 is provided. This source control device 10 ensures that the X-ray flux of the X-ray radiation emitted by the X-ray source 2 is modulated during the detection intervals such that in each detection interval, during which a detection signal is acquired (i.e. the time interval during which a single detection signal is acquired from a fixed angular position of the X-ray source or from a small angular range) the x-ray flux level at the beginning of the detection interval is so low that no detector cell 61 is saturated. In particular, the X-ray flux level is so low that detection elements that are subjected to the direct X-ray beam, i.e. at the peripheries of the detector 6 where the X-ray beam is not passing through the object, are not saturated by said low X-ray flux level at the beginning of the detection interval. Thereafter, the X-ray flux is increased, for instance, according a linear function as shown in FIG. 6.

The examination device further comprises a detection control device 11 for evaluating the detection signals acquired by the detector cells 61 of the detector 6. Preferably, for each detector cell 61 a separate detection control unit is provided. However, it is also possible that only for selected detector cells 61 separate detection control units are provided. Further, it is also possible that groups of detector cells are combined and that for such a group a separate detection control unit is provided for evaluation of the combined detection signals for the purpose of saturation detection.

Figure 2:
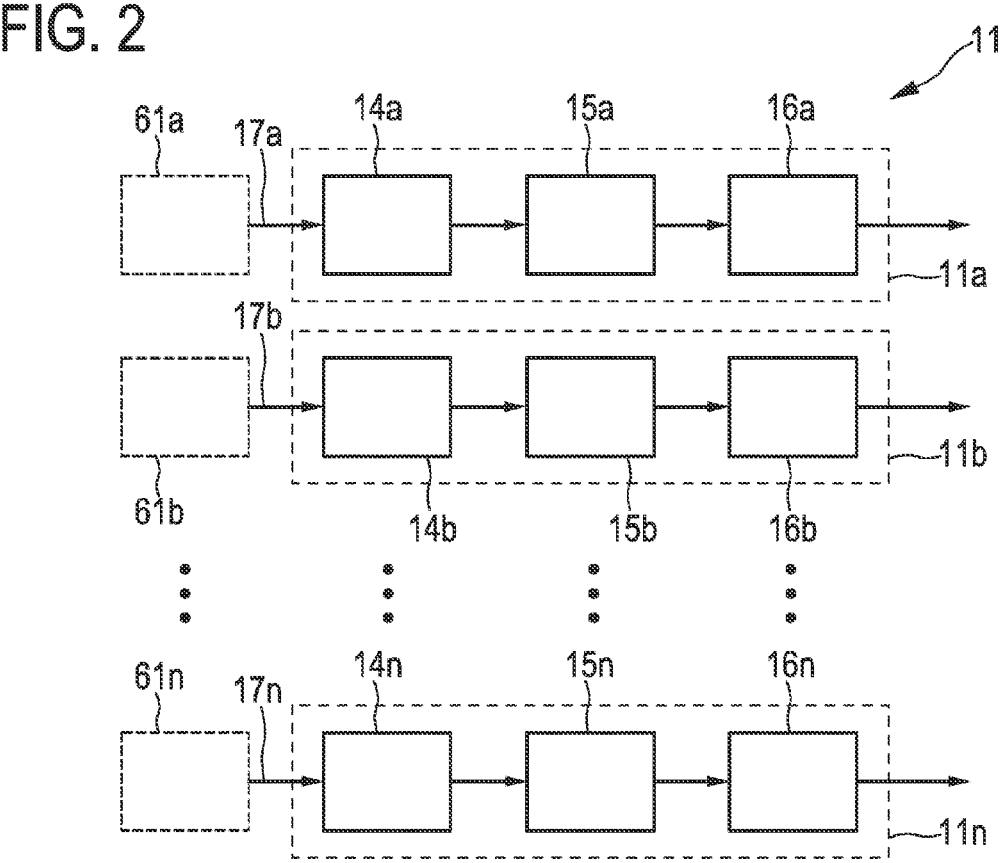
FIG. 2 shows a block diagram of an embodiment of detection control device.

An embodiment of the detection control device 11 is shown in FIG. 2. In the illustrated example n detection control units 11*a*, 11*b*, . . . , 11*n* are provided for individual detector cells 61*a*, 61*b*, . . . , 61*n*, preferably for detector cells at the peripheries of the detector 6 having the highest likelihood to go into saturation. Thus, n detection channels 17*a*, 17*b*, . . . , 17*n* are provided by such detection control units 11*a*-11*n*. Each detection control unit 11*a*-11*n* has its own saturation detection unit 14*a*, 14*b*, . . . , 14*n* for detecting, during a detection interval, saturation at the respective detector cell 61*a*-61*n*. Further, each detection control unit 11*a*-11*n* comprises an individual detection stopping unit 15*a*, 15*b*, . . . , 15*n* for stopping detection of X-ray radiation at the respective detector cell 61*a*-61*n* for the remaining time of the detection interval.

In other words, if the saturation is detected at a particular detector cell the detection stopping unit of said detection channel stops further detection of radiation in said detection channel from that moment on up to the end of the detection interval since any detected signals from that moment on by a saturated detector cell do anyhow not reflect the actual radiation incident on said detector cell. This stopping is particularly made by stopping to register and/or evaluate any signal that comes from the saturated detector cell, i.e. said signal is simply ignored, but only the detection signal outputted by the detector cell up to the moment of saturation is registered for further processing.

Each detection control unit 11*a*-11*n* further comprises a time measuring unit 16*a*, 16*b*, . . . , 16*n* for obtaining a time information that indicates the effective time portion of the detection interval during which X-ray radiation has been detected by their respective detector cell 61*a*-61*n* without saturation. In other words, the time is measured during which the respective detector cell has not been saturated, which inherently includes the information for how much time of the whole detection interval the detector cell has been saturated.

Figure 3:
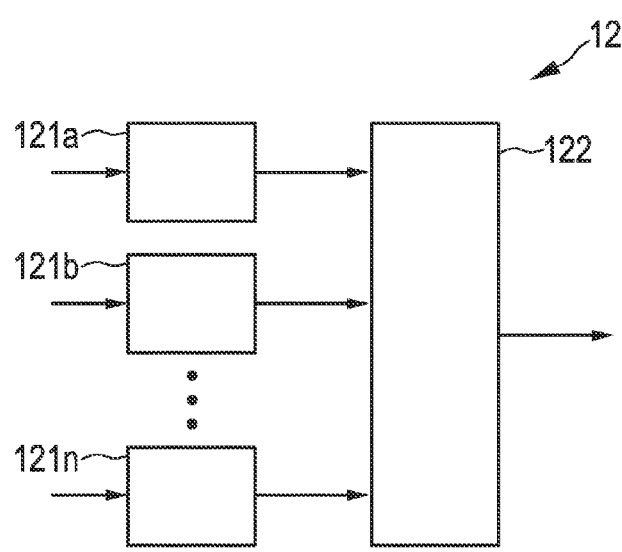
FIG. 3 shows a block diagram of an embodiment of a signal processing device.

The detection signals and, if applicable, any time information measured by the detection control device 11 is then provided to a signal processing device 12 for reconstructing an X-ray image based on the detection signals. Similarly as with the detection control device 11 the signal processing device 12 preferably comprises a number of signal correction units 121*a*-121*n* as illustrated in FIG. 3, wherein the number of signal correction units 121*a*-121*n* generally corresponds to the number of detection control units 11*a*-11*n*. Therein the detection signals of detector cells which have come into saturation are not processed directly as the detections signals outputted from unsaturated detector cells, but are corrected in advance based on the acquired time information belonging to said detection signal. This correction will be explained below in more detail. The detection signal, both from unsaturated detector cells (uncorrected) and from saturated detector cells (corrected) are then provided to a signal processing unit 122, e.g. for reconstructing an x-ray image therefrom.

The reconstructed image is then be issued by the signal processing device 12, for instance to a display 13 for displaying the obtained image.

For overall control of the examination it is preferred that not only the motors 7, 8, but also the source control device 10, the detection control device 11, the signal processing device 12, and the detector 6 itself the are controlled by the control device 9.

Figure 4:
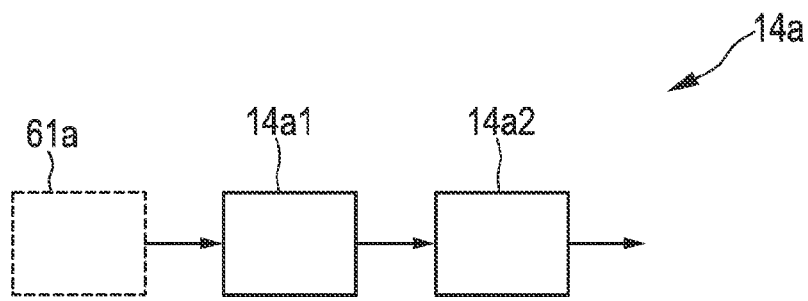
FIG. 4 shows a block diagram of an embodiment of saturation detection device.

An embodiment of a saturation detection unit 14*a* is shown in FIG. 4. Accordingly, the saturation detection unit 14*a* comprises a current measuring unit 14*a*1 for measuring the detector current, in particular the mean detector current, at the output of the associated detector cell 61*a*. Further, it comprises a comparator 14*a*2 for comparing the measured detector current to a reference current indicating saturation. Said reference current is known and can be acquired in advance for the respective detector, e.g. by the manufacturer of the detector. Alternatively, the manufacturer of the examination device can obtain these reference currents, e.g. by calibration measurements or separate measurements for acquiring said reference currents. For instance, for each individual detector cell an individual reference current can be acquired which reflects the current at which the detector cell goes into saturation. However, it is also possible that a single reference current (e.g. a mean reference current) is obtained that is applied for detecting saturation for all detector cells, or that reference currents are provided for various groups of detector cells.

By use of the comparator 14*a*2 it is then detected whether the output current of the associated detector cell 61*a* exceeds the reference current. If this is the case the comparator 14*a*2 issues a respective output signal to the associated detection stopping unit 15*a* to stop further registration of the detection signal on this detection channel.

The time measuring units 16*a*-16*n* can be simple elements like simple counters counting the proportion of the detection signal that has already passed. However, other implementations are possible that allow such a time registration. For instance, the detection interval could be sub-divided into smaller sub-intervals, and at the end of each sub-interval it is checked if there is an overload at the assigned detector cell. To give an example, 10 sub-intervals shall be assumed, and if at the end of sub-interval "n" an overload is detected, the detection signal of the first "n−1" intervals is summed up ($=N_{SAT}$), and the time $t_{SAT}$ until overload is then determined by $t_{SAT}=\Delta/10(n-1)$, wherein $\Delta$ is the time duration of the complete detection interval.

Figure 5:
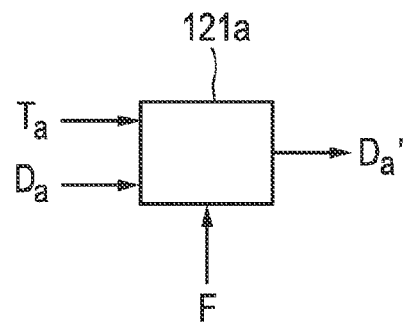
FIG. 5 shows a block diagram of an embodiment of a signal processing unit.

An embodiment of a signal processing unit 121a is shown in FIG. 5. As illustrated, the signal processing device 121a obtains, as an input information, the time information $T_a$ obtained by the respective time measuring unit 16a, the detection signal $D_a$ acquired by the respective detector cell 61a, eventually limited due to the stopped registration because of saturation of the detector cell 61a, and the known flux modulation function F that is applied in a source control unit 10 for modulating the X-ray flux during the detection interval. The output of the signal processing unit 121a is again a detection signal $D_a'$ which corresponds, when the respective detector cell 61a did not go into saturation, to the completely measured detection signal $D_a$, and which is a corrected detection signal if the respective detector cell 61a did go into saturation. All these outputted detector signals D' are then processed further by the image reconstruction unit 122 in which, using common knowledge for reconstructing images from detection signals, an image is reconstructed as desired or a (2D or 3D) data set is generated.

A possible way of correcting detection signals shall be illustrated with reference to FIG. 6 showing, as an example, a saw-tooth like function over time t according to which the X-ray flux I(t) is modulated during each detector interval having a duration $\Delta$.

Within the detection interval $\Delta$ the intensity (photons per unit time) vary from $I_0$ to $mI_0$ with m being the defined modulation depth, $$I(t) = I_0 + I_0(m-1)\frac{t}{\Delta}.$$

The number of detected photons in the interval 0 . . . t is $$N = \int_0^t I(t)\,dt = I_0 t + 0.5 I_0 t^2 \frac{m-1}{\Delta}.$$

If the detector runs into saturation $$I(t_{SAT}) = I_{SAT}$$

at $t_{SAT}$, with $N_{SAT}$ detected photons, the above equation can be used to estimate $$I_0 = \frac{N_{SAT}}{t_{SAT} + 0.5 t_{SAT}^2 (m-1)\Delta^{-1}}.$$

Knowing $I_0$ the total amount of photons $$N_{TOTAL} = I_0 \Delta \left(1 + \frac{m-1}{2}\right) = \frac{N_{SAT}\Delta\left(1 + \frac{m-1}{2}\right)}{t_{SAT} + 0.5 t_{SAT}^2 (m-1)\Delta^{-1}}$$

can be estimated.

Various methods can be applied to modulate the X-ray flux. This can in principle be achieved, for instance, by modulation the source current or changing the X-ray tube filament current using various filaments with individual grid switches, and/or using multiple tubes. Further, the idea of fast dose modulation using z-deflection in a rotating anode or a rotating frame tube as described in WO 2008/155715 A2 can be used.

The invention applies primarily to photon counting X-ray detectors based on single layer or multiple layer (3D) structured photon-counting detectors, operated under conditions of ultra-high X-ray fluxes, like, e.g., medical X-ray CT, pre-clinical CT, or CT for material inspection or security applications. It allows reconstructing images of essentially the same quality as a detector with unlimited count rate performance.

By use of the invention, a better image quality can be finally obtained. Only those detection signals which are outputted by detector cells that run into saturation are modified compared to the actual detection signals. Using a correction of those detection signals based on a time measurement during which the respective detector cells have run into saturation, a high accuracy can be obtained contributing to the desired quality of reconstructed images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An x-ray examination device comprising:
   an X-ray source for emitting an X-ray beam of X-ray radiation while rotating around an imaging region,
   an X-ray detector having a plurality of detector cells for detecting X-ray radiation emitted by said X-ray source and having passed through said imaging region and for outputting detection signals,
   a source control unit for modulating an X-ray flux during detection intervals, starting at a beginning of a detection interval with an X-ray flux level that avoids saturation of the X-ray detector in a direct X-ray beam and thereafter increasing the X-ray flux,
   a detection control unit for evaluating said detection signals, the detection control unit comprising:
   i) a saturation detection unit for detecting, during the detection interval, saturation at predetermined detector cells and/or groups of detector cells, ii) a detection stopping unit for stopping detection of X-ray radiation at saturated detector cells or groups of detector cells for a remaining time of the detection interval, and iii) a time measuring unit for obtaining a time information indicating an effective time portion of the detection interval during which X-ray radiation has been detected without saturation, and a signal processing device for reconstructing an X-ray image based on the detection signals, wherein detection signals of detector cells and/or groups of detector cells at which detection of X-ray radiation has been stopped during the detection interval due to saturation are corrected using the time information.

2. The x-ray examination device as claimed in claim 1, wherein said source control unit is adapted for modulating the X-ray flux in such a manner that the X-ray flux continuously increases over time during a detection interval.

3. The x-ray examination device as claimed in claim 1, wherein said source control unit is adapted for modulating the X-ray flux of said X-ray source according to a saw-tooth like function.

4. The x-ray examination device as claimed in claim 1, wherein said X-ray detector is a photon-counting X-ray detector.

5. The x-ray examination device as claimed in claim 1, wherein said detection control unit comprises a plurality of detection control sub-units for a plurality of individual detector cells and/or groups of detector cells, in particular for individual detector cells and/or groups of detector cells at peripheries of the X-ray detector.

6. The x-ray examination device as claimed in claim 1, wherein said detection control unit comprises a detection control sub-unit for each detector cell.

7. The x-ray examination device as claimed in claim 1, wherein said saturation detection unit comprise a current measuring unit for measuring the detector current, in particular mean detector current, at the output of a detector cell or a group of detector cells, and a comparator for comparing the detector current to a reference current indicating saturation.

8. The x-ray examination device as claimed in claim 1, wherein said detection stopping unit is adapted for registering and/or evaluating a detection signal from a saturated detector cell or group of detector cells.

9. The x-ray examination device as claimed in claim 1, wherein said signal processing device is adapted for correcting a detection signal of a detector cell and/or a group of detector cells, at which detection of X-ray radiation has been stopped during the detection interval, by estimating a missing detection signal portion of the detection signal for the remaining time of the detection interval of the detection interval, during which the X-ray radiation has not been detected, based on a known flux modulation function, measured detection signal portion and the time information obtained for this detection signal.

10. An x-ray examination method comprising the steps of:
emitting an X-ray beam of X-ray radiation while rotating around an imaging region;
detecting X-ray radiation having passed through said imaging region and outputting detection signals by an X-ray detector having a plurality of detector cells;
modulating X-ray flux during detection intervals, starting at a beginning of a detection interval with an X-ray flux level that avoids saturation of the X-ray detector in a direct X-ray beam and thereafter increasing the X-ray flux;

evaluating said detection signals, wherein the evaluating comprises:
i) detecting, during the detection interval, saturation at predetermined detector cells and/or groups of detector cells,
ii) stopping detection of X-ray radiation at saturated detector cells or groups of detector cells for a remaining time of the detection interval, and
iii) obtaining a time information indicating an effective time portion of the detection interval during which X-ray radiation has been detected without saturation; and
reconstructing an X-ray image based on the detection signals, wherein detections signals of detector cells and/or groups of detector cells at which detection of X-ray radiation has been stopped during a detection interval due to saturation are corrected using the time information.

11. The x-ray examination method as claimed in claim 10, wherein modulating X-ray flux continuously increases over time during the detection interval.

12. The x-ray examination method as claimed in claim 10, wherein modulating X-ray flux is based on a saw-tooth function.

13. The x-ray examination method as claimed in claim 10, further comprising measuring mean detector current and comparing the detector current to a reference current indicating saturation.

14. The x-ray examination method as claimed in claim 10, further comprising registering and evaluating a detection signal from a saturated detector cell or group of detector cells.

15. The x-ray examination method as claimed in claim 10, further comprising correcting a detection signal of at least one of a detector cell and a group of detector cells, at which detection of X-ray radiation has been stopped during the detection interval, by estimating a missing detection signal portion of the detection signal for the remaining time of the detection interval of the detection interval, during which the X-ray radiation has not been detected, based on a known flux modulation function, measured detection signal portion and the time information obtained for this detection signal.

16. A non-transitory computer readable medium encoded with a computer program comprising program code means for causing a computer to control an X-ray examination device comprising an X-ray source for emitting an X-ray beam of X-ray radiation while rotating around an imaging region, and an X-ray detector having a plurality of detector cells for detecting X-ray radiation emitted by said X-ray source and having passed through said imaging region and for outputting detection signals, said computer program comprising program code means to control the X-ray examination device to:
modulate X ray flux during detection intervals, starting at a beginning of a detection interval with an X-ray flux level that avoids saturation of the X-ray detector in a direct X-ray beam and thereafter increasing the X-ray flux,
evaluate said detection signals, the evaluation comprising the steps of:
i) detecting, during a detection interval, saturation at predetermined detector cells and/or groups of detector cells,
ii) stopping detection of X-ray radiation at saturated detector cells or groups of detector cells for a remaining time of the detection interval, and iii) obtaining a time information indicating an effective time portion of the detection interval during which X-ray radiation has been detected without saturation, and reconstruct an X-ray image based on the detection signals, wherein detections signals of detector cells and/or groups of detector cells at which detection of X-ray radiation has been stopped during a detection interval due to saturation are corrected using the time information.

* * * * *